United States Patent
Chen et al.

(10) Patent No.: US 12,272,028 B2
(45) Date of Patent: Apr. 8, 2025

(54) MAGNETIC RESONANCE IMAGING SYSTEM AND METHOD, AND COMPUTER-READABLE STORAGE MEDIUM

(71) Applicant: GE Precision Healthcare LLC, Wauwatosa, WI (US)

(72) Inventors: Fuqiang Chen, Beijing (CN); Kun Wang, Beijing (CN); Bohao Li, Beijing (CN); Liya Ma, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 382 days.

(21) Appl. No.: 17/844,288

(22) Filed: Jun. 20, 2022

(65) Prior Publication Data

US 2023/0036285 A1 Feb. 2, 2023

(30) Foreign Application Priority Data

Jul. 28, 2021 (CN) .......................... 202110857678.1

(51) Int. Cl.
*G06T 5/50* (2006.01)
*A61B 5/00* (2006.01)
(Continued)

(52) U.S. Cl.
CPC ................ *G06T 5/50* (2013.01); *A61B 5/055* (2013.01); *A61B 5/7203* (2013.01); *A61B 5/7267* (2013.01); *G01R 33/5608* (2013.01); *G06T 5/70* (2024.01); *G06T 7/0012* (2013.01); *G06T 7/70* (2017.01); *G06T 2207/10088* (2013.01);
(Continued)

(58) Field of Classification Search
CPC .................. A61B 5/055; A61B 5/7203; G06T 2207/20221; G06T 2207/10088; G06T 5/70

See application file for complete search history.

(56) References Cited

U.S. PATENT DOCUMENTS

| 6,242,914 | B1 * | 6/2001 | Yoshitome | G01R 33/5615 |
| | | | | 324/309 |
| 11,360,180 | B2 * | 6/2022 | Yap | G01R 33/56509 |

(Continued)

OTHER PUBLICATIONS

Kim et al, MRI Artifact Cancellation due to Unknown Respiratory Motion, IEEE Explore, Feb. 12, 2007.*

(Continued)

*Primary Examiner* — Molly Wilburn
*Assistant Examiner* — Jordan McKenzie Elliott

(57) ABSTRACT

Provided in the present invention are a magnetic resonance imaging system and method, and a computer-readable storage medium. The method comprises: performing a medical scan of a subject and acquiring a first medical image having a first noise interference artifact, and performing an additional scan of the subject to acquire a second medical image, wherein the second medical image has a second noise interference artifact, and the location mapping of the second noise interference artifact in the first medical image is symmetrical to the location of the first noise interference artifact relative to a pixel center of the first medical image; and performing synthesis-related processing on the first medical image and the second medical image to acquire a post-processed image with reduced noise interference artifacts.

20 Claims, 11 Drawing Sheets

(51) Int. Cl.
    *A61B 5/055*     (2006.01)
    *G01R 33/56*     (2006.01)
    *G06T 5/70*     (2024.01)
    *G06T 7/00*     (2017.01)
    *G06T 7/70*     (2017.01)

(52) U.S. Cl.
    CPC ............... *G06T 2207/20081* (2013.01); *G06T 2207/20084* (2013.01); *G06T 2207/20221* (2013.01); *G06T 2207/30004* (2013.01); *G06T 2207/30168* (2013.01)

(56) References Cited

U.S. PATENT DOCUMENTS

| | | | | |
|---|---|---|---|---|
| 2010/0290689 | A1* | 11/2010 | Gupta | G06T 7/11 382/131 |
| 2016/0077175 | A1* | 3/2016 | Mori | G01R 33/56 324/321 |
| 2016/0103195 | A1* | 4/2016 | Zuehlsdorff | G01R 33/543 324/309 |
| 2020/0111194 | A1* | 4/2020 | Wang | G06N 3/047 |
| 2021/0082092 | A1* | 3/2021 | Sargent | G06T 5/50 |
| 2021/0103017 | A1* | 4/2021 | Dyvorne | G01R 33/288 |
| 2021/0177296 | A1* | 6/2021 | Saalbach | G16H 30/40 |
| 2022/0065967 | A1* | 3/2022 | Wang | G01R 33/56518 |
| 2022/0091208 | A1* | 3/2022 | He | G01N 24/08 |
| 2022/0254050 | A1* | 8/2022 | Smirnov | G06T 7/90 |
| 2022/0326329 | A1* | 10/2022 | Dong | G01R 33/56545 |
| 2022/0413074 | A1* | 12/2022 | Nehrke | G06N 3/084 |
| 2023/0236271 | A1* | 7/2023 | Fessler | G01R 33/5608 324/309 |

OTHER PUBLICATIONS

Heiland, "From A as in Aliasing to Z as in Zipper: Artifacts in MRI." Clin Neuroradiol 18, 25-36 (2008), 12 pages.

Jin et al., "MRI artifact correction using sparse + low-rank decomposition of annihilating filter-based hankel matrix". Magn Reson Med. 2017;78(1):327-340, 14 pages.

* cited by examiner

MAGNETIC RESONANCE IMAGING SYSTEM AND METHOD, AND COMPUTER-READABLE STORAGE MEDIUM

CROSS REFERENCE

The present application claims priority and benefit of Chinese Patent Application No. 202110857678.1 filed on Jul. 28, 2021, which is incorporated herein by reference in its entirety.

FIELD OF THE INVENTION

The present invention relates to the field of medical imaging, and in particular to a magnetic resonance imaging (MRI) system and method and a computer-readable storage medium.

BACKGROUND OF THE INVENTION

A magnetic resonance imaging system, while performing a scan of an examined subject, excites imaged tissue to produce a magnetic resonance signal, and this magnetic resonance signal is acquired and reconstructed as a magnetic resonance image.

Artifacts of specific shapes resulting from radio-frequency interference noise sometimes appear in magnetic resonance images. In the prior art, it is necessary to first identify the source of the artifacts in order to remove the specific interference, which is complicated and time-consuming.

BRIEF DESCRIPTION OF THE INVENTION

An aspect of the present invention provides a magnetic resonance imaging method, comprising: performing a medical scan of a subject and acquiring a first medical image having a first noise interference artifact, and performing an additional scan of the subject to acquire a second medical image. The second medical image has a second noise interference artifact, and the location mapping of the second noise interference artifact in the first medical image is symmetrical to the location of the first noise interference artifact relative to a pixel center of the first medical image. The method further includes performing synthesis-related processing on the first medical image and the second medical image to acquire a post-processed image with reduced noise interference artifacts.

Another aspect of the present invention further provides a computer-readable storage medium comprising a stored computer program, wherein the aforementioned method is performed when the computer program is run.

Another aspect of the present invention further provides a magnetic resonance imaging system, comprising: a scanner and a controller used to control the scanner to perform a magnetic resonance scan. The magnetic resonance scan comprises: performing a medical scan of a subject and acquiring a first medical image, wherein the first medical image has a first noise interference artifact; and performing an additional scan of the subject to acquire a second medical image, wherein the second medical image has a second noise interference artifact. The location mapping of the second noise interference artifact in the first medical image is symmetrical to the location of the first noise interference artifact relative to a pixel center of the first medical image. The magnetic resonance imaging system further includes an image processor to perform synthesis-related processing on the first medical image and the second medical image to acquire a post-processed image with reduced noise interference artifacts.

It should be understood that the brief description above is provided to introduce, in simplified form, some concepts that will be further described in the Detailed Description. The brief description above is not meant to identify key or essential features of the claimed subject matter. The scope is defined uniquely by the claims that follow the detailed description. Furthermore, the claimed subject matter is not limited to implementations that solve any disadvantages noted above or in any section of the present disclosure.

BRIEF DESCRIPTION OF THE DRAWINGS

The present invention will be better understood by reading the following description of non-limiting embodiments with reference to the accompanying drawings, wherein.

DETAILED DESCRIPTION

Specific implementations of the present invention will be described below. It should be noted that in the specific description of these embodiments, for the sake of brevity and conciseness, this specification may not describe all features of the actual implementations in detail. It should be understood that in the actual implementation process of any implementations, just as in the process of any engineering project or design project, a variety of specific decisions are often made to achieve specific goals of the developer and to meet system-related or business-related constraints, which may also vary from one implementation to another. Furthermore, it should also be understood that although efforts made in such development processes may be complex and tedious, for those of ordinary skill in the art related to the disclosure of the present invention, some design, manufacture or production changes based on the technical content disclosed in the present disclosure are only common technical means, and should not be construed as insufficient content of the present disclosure.

Unless otherwise defined, the technical or scientific terms used in the claims and the description are as they are usually understood by those of ordinary skill in the art to which the present invention pertains. Terms such as "first," "second," and similar words used in this specification and claims do not denote any order, quantity, or importance, but are only intended to distinguish different constituents. The terms "one" or "a/an" and similar terms do not denote a limitation of quantity, but rather the presence of at least one. The terms "include" or "comprise" and similar terms mean that an element or article in front of "include" or "comprise" encompass elements or articles and their equivalent elements listed after "include" or "comprise", and do not exclude other elements or articles. The term "connect" or "connected" and similar words are not limited to physical or mechanical connections, and are not limited to direct or indirect connections.

Figure 1:
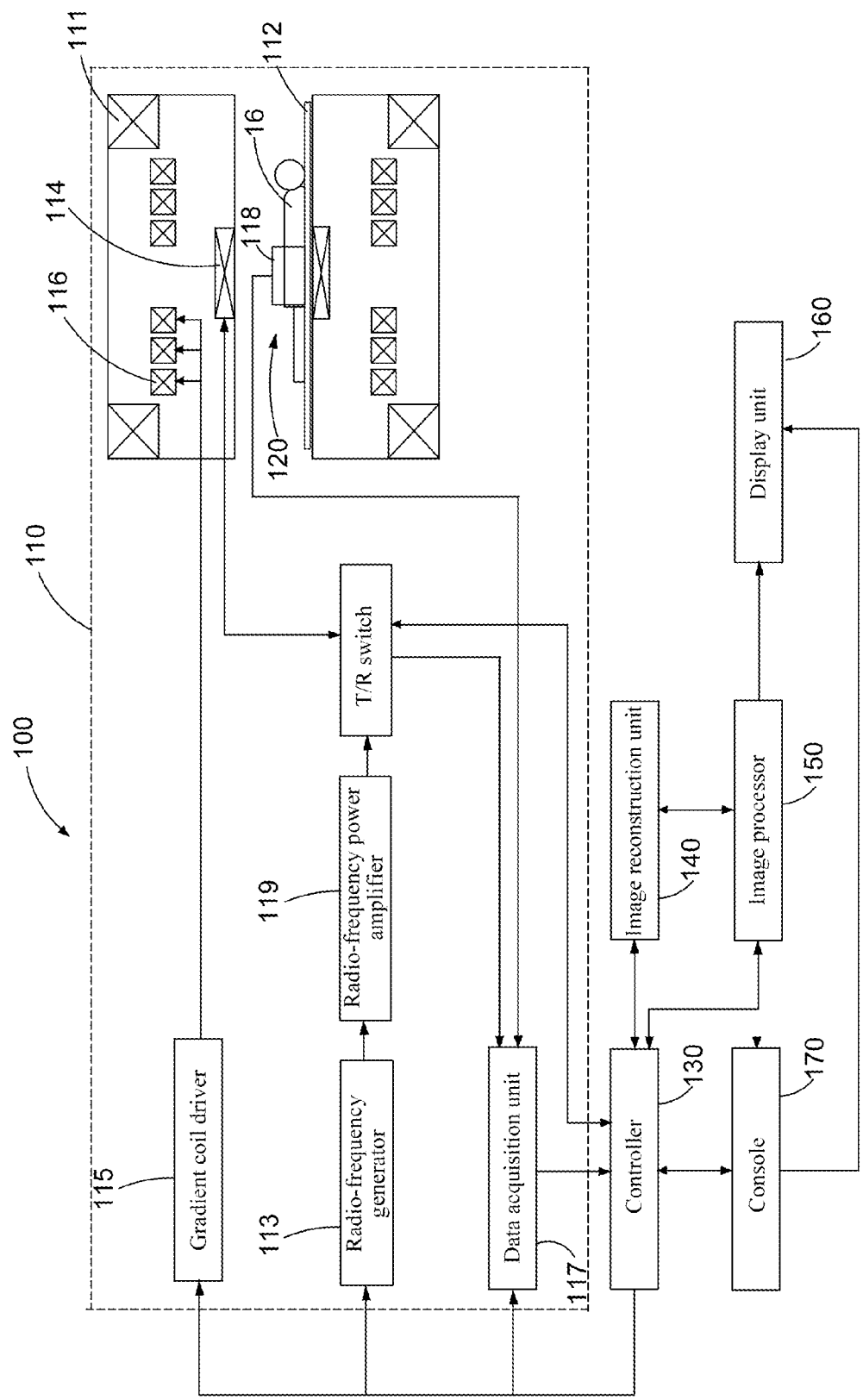
FIG. 1 illustrates a schematic structural diagram of a magnetic resonance imaging system according to some embodiments of the present invention.

FIG. 1 illustrates a schematic structural diagram of a magnetic resonance imaging (MRI) system according to some embodiments of the present invention. The magnetic resonance imaging system 100 includes a scanner 110. The scanner 110 is used to perform a magnetic resonance scan of a subject (e.g., a human body) 16 to generate image data of a region of interest of the subject 16, wherein the region of interest may be a pre-determined anatomical site or anatomical tissue.

The magnetic resonance imaging system 100 may include a controller 130 coupled to the scanner 110 so as to control the scanner 110 to perform the aforementioned magnetic resonance scanning procedure.

In an example, the scanner 110 may include a main magnet assembly 111, a table 112, a radio-frequency generator 113, a radio-frequency power amplifier 119, a radio-frequency transmitting coil 114, a surface coil 118, a gradient coil driver 115, a gradient coil assembly 116, and a data acquisition unit 117.

The main magnet assembly 111 usually includes an annular superconducting magnet defined in a housing. The annular superconducting magnet is mounted in an annular vacuum container. The annular superconducting magnet and the housing thereof define a cylindrical space surrounding the subject 16, such as a scanning chamber 120 shown in FIG. 1. The main magnet assembly 111 generates a constant magnetic field, i.e., a B0 field, in a Z direction of the scanning chamber 120. Typically, a uniform portion of the B0 field is formed in a central region of the main magnet.

The table 112 is configured to carry the subject 16, and travel in the Z direction to enter or exit the aforementioned scanning chamber 120 in response to the control of the controller 130. For example, in one embodiment, an imaging volume of the subject 16 may be positioned in a central region of the scanning chamber with uniform magnetic field strength so as to facilitate scanning imaging of the imaging volume of the subject 16.

The Z direction is typically the direction extending from the head to the feet (or from the feet to the head) when the subject 16 is positioned on the table 112. For example, a selected layer may be a slice at any position in the Z direction.

The magnetic resonance imaging system 100 uses the formed B0 field to transmit a static magnetic field to the subject 16 located in the scanning chamber, so that protons in a resonant region in the body of the subject 16 precess in an ordered manner to generate a longitudinal magnetization vector.

The radio-frequency generator 113 is configured to generate a radio-frequency pulse, such as a radio-frequency excitation pulse, in response to a control signal of the controller 130. The radio-frequency power amplifier 119 is configured to amplify a low-power radio-frequency signal generated by the radio-frequency generator 113 to generate a high-power radio-frequency signal that may excite the human tissue. The high-power radio-frequency signal can be input to the radio-frequency transmitting coil 114 via a radio-frequency transmitting line, so that the radio-frequency transmitting coil 114 transmits a radio-frequency field B1 orthogonal to the B0 field to the subject 16 to excite atomic nuclei in the aforementioned resonant region to generate a transverse magnetization vector.

The radio-frequency transmitting coil 114 may include, for example, a body coil disposed along an inner circumference of the main magnet, or a local coil dedicated to local imaging.

After the radio-frequency excitation pulse ends, the proton group becomes out-of-phase, the macroscopic transverse magnetization vector in the tissue gradually decays, a free induction decay signal, namely, a magnetic resonance signal that can be acquired, is generated during the process in which the transverse magnetization vector of the subject 16 is gradually restored to zero.

The gradient coil driver 115 is configured to provide a suitable current/power to the gradient coil assembly 116 in response to a gradient pulse control signal or a shimming control signal sent from the controller 130.

The gradient coil assembly 116, on one hand, forms a varying magnetic field in an imaging space so as to provide three-dimensional location information for the aforementioned magnetic resonance signal, and on the other hand generates a compensating magnetic field of the B0 field to shim the B0 field.

The gradient coil assembly 116 may include three gradient coils, which are respectively configured to generate magnetic field gradients inclined to three spatial axes (for example, the X-axis, Y-axis, and Z-axis) perpendicular to each other. More specifically, the gradient coil assembly 116 applies a magnetic field gradient in the slice selection direction (e.g., Z-direction) to vary the field strength in the region such that the precession frequencies of protons of the imaged tissue in different layers of the region are different, so as to achieve layer selection. Those skilled in the art understand that the layer is any one of a plurality of two-dimensional slices distributed in the Z direction in the three-dimensional imaging volume. When this imaging area is scanned, the radio-frequency transmitting coil 114 responds to the aforementioned radio-frequency excitation signal, then a layer having a precession frequency corresponding to this radio-frequency excitation signal is excited. The gradient coil assembly 116 applies a magnetic field gradient in the phase encoding direction (e.g., Y-direction) and the frequency encoding direction (e.g., X-direction), respectively, such that the magnetic resonance signals of the excited layers have different phases and frequencies, thereby achieving phase encoding and frequency encoding.

The aforementioned radio-frequency transmitting coil 114 may be connected to a transmitting/receiving (T/R) switch. The transmitting/receiving switch is controlled so that the body coil may be switched between a transmitting mode and a receiving mode. In the receiving mode, the radio-frequency transmitting coil may be configured to receive a magnetic resonance signal from the subject 16.

The surface coil 118 is usually arranged close to a scan part (region of interest) of the subject 16 (for example, covering or laying on the body surface of the subject 16), and the surface coil 118 is also configured to receive a magnetic resonance signal from the subject 16.

The data acquisition unit 117 is configured to acquire the aforementioned magnetic resonance signal (for example, received by the body coil or the surface coil) in response to a data acquisition control signal of the controller 130. In one embodiment, the data acquisition unit 117 may include, for example, a radio-frequency preamplifier, a phase detector, and an analog/digital converter, where the radio-frequency preamplifier is configured to amplify the magnetic resonance signal, the phase detector is configured to perform phase detection on the amplified magnetic resonance signal, and the analog/digital converter is configured to convert the phase-detected magnetic resonance signal from an analog signal to a digital signal.

The data acquisition unit 117 is further configured to respond to a data storage control signal of the controller 130 to store this digitized magnetic resonance signal (or echo) in k-space. The k-space is a populated space of raw data of magnetic resonance signals with spatial positioning encoding information. The data acquisition unit 117 fills signals with different phase information and frequency information in the corresponding locations in the k-space according to a predetermined data filling method. In one example, the two-dimensional k-space may include a frequency-encoding line Kx and a phase-encoding line Ky. The data acquisition at each level may contain multiple signal acquisition cycles (or repetition times TR), and each signal acquisition cycle may correspond to one change in the magnetic field gradient (incremental or decremental) in the phase-encoding direction (i.e., one signal acquisition is performed for each phase encoding gradient applied), and the magnetic resonance signal acquired in each signal acquisition cycle is filled into a frequency-encoding line Kx. Through multiple signal acquisition cycles, multiple frequency encoding lines having different phase information may be filled, and each acquired magnetic resonance signal has multiple decomposition frequencies.

Those skilled in the art could understand that when imaging scanning is performed on the subject 16, the controller 130 can use a sequence generator (not shown in the figure) to send sequence control signals to the aforementioned components (for example, the radio-frequency generator 113, the gradient coil driver 115, etc.) of the scanner 110, so that the scanner 110 performs a preset scanning sequence.

Those skilled in the art could understand that the "scan sequence" refers to a combination of pulses having specific amplitudes, widths, directions, and time sequences and applied when a magnetic resonance imaging scan is performed. The pulses may typically include, for example, a radio-frequency pulse and a gradient pulse. The radio-frequency pulses may include, for example, radio-frequency transmission pulses, radio-frequency refocus pulses, inverse recovery pulses, etc. The gradient pulses may include, for example, the aforementioned gradient pulse used for layer selection, gradient pulse used for phase encoding, gradient pulse used for frequency encoding, etc. Typically, a plurality of scanning sequences can be pre-set in the magnetic resonance system, so that the sequence suitable for clinical detection requirements can be selected. The clinical detection requirements may include, for example, a part to be imaged, an imaging function, an imaging effect, and the like.

Performing a magnetic resonance scan of the subject 16 may include a positioning scan (three-plane scan) and a formal scan. One or more scanning sequences may be performed during the positioning scan and formal scan. During the positioning scan, at least one of a coronal positioning image, a sagittal positioning image, and a transverse section positioning image of the subject may be acquired, and scan parameters of the formal scan, such as the scan range of the formal scan, are determined on the basis of this positioning image. Typically, formal scans are performed on subjects to acquire medical images that may be used for clinical diagnosis.

In a single magnetic resonance examination for one subject 16, the positioning image acquired from the positioning scan may be a prior-scan image acquired prior to the formal scan. The controller 130 may also increase/reduce/adjust the scan sequences in response to different process settings selected by the user on the basis of different clinical applications.

Prior to performing one or more scan sequences of the positioning scan or formal scan, a pre-scan may be performed, and during the pre-scan, pre-setting of the system may be completed. For example, frequency adjustment may be performed to determine the Larmor frequency of proton resonance or (the center frequency of this magnetic resonance examination) for the present scan on the basis of the feedback of magnetic resonance signals at different frequencies, and radio-frequency transmission intensity adjustment may be performed to determine the radio-frequency transmission power for the present scan on the basis of the feedback of magnetic resonance signals at different radio-frequency transmission intensities. It is also possible to acquire a pre-scan image on the basis of a pre-scan of the subject, and to analyze and adjust the uniformity of the main magnetic field on the basis of the pre-scan image, so as to achieve shimming configuration. The pre-scan image may be a prior-scan image acquired before performing the aforementioned positioning scan or formal scan.

The magnetic resonance imaging system 100 may include an image reconstruction unit 140, which is configured to perform an inverse Fourier transform on data stored in the k-space to reconstruct a three-dimensional image or a series of two-dimensional slice images of the imaging volume of the subject 16. Specifically, the image reconstruction unit 140 may perform the aforementioned image reconstruction on the basis of communication with the controller 130.

The magnetic resonance imaging system 100 may include an image processor 150, which may perform any required image post-processing on the aforementioned three-dimensional image or any image in an image sequence. The post-processing may be an improvement or adaptive adjustment made to an image in any aspect of contrast, uniformity, sharpness, brightness, artifacts, etc. In one example, the image processor 150 may include a trained deep learning network, or a unit that communicates with the trained neural network. The image processor 150 may also perform image processing on the basis of communication with the controller 130.

In one embodiment, the controller 130, the image reconstruction unit 140, and the image processor 150 may separately or collectively include a computer processor and a storage medium. The storage medium records a predetermined data processing program to be executed by the computer processor. For example, the storage medium may store a program used to implement scanning processing, image reconstruction, image processing, etc. For example, the storage medium may store a program used to implement the method of magnetic resonance imaging according to an embodiment of the present invention. The storage medium may include, for example, a ROM, a floppy disk, a hard disk, an optical disk, a magneto-optical disk, a CD-ROM, or a non-volatile memory card.

The magnetic resonance imaging system 100 may include a display unit 160, which may be used to display an operation interface and various data, images, or parameters generated in the image acquisition and processing processes.

The magnetic resonance imaging system 100 includes an operation console 170, which may include user input devices, such as a keyboard, a mouse, etc. The controller 130 may communicate with the scanner 110, the image reconstruction unit 140, the image processor 150, the display unit 160, etc., in response to a control command generated by a user on the basis of the operation console 170 or an operation panel/button, etc., disposed on the housing of the main magnet.

Radio-frequency interference signals from the outside of a magnetic resonance system may be captured during the acquisition of a magnetic resonance signal, resulting in a noise interference image in the reconstructed image, and such a noise interference image may include, for example, chain-shaped artifacts.

Radio-frequency shielding devices may be used to isolate the interference of the external environment on the image signal, thus reducing the aforementioned artifacts. However, the causes for the aforementioned artifacts may be of all sorts, such as insufficient shielding between scans, gaps in the shielding layer of the equipment, or the introduction of external radio-frequency interferences due to the failure to close the door of the magnetic resonance room, etc.

To reduce such artifacts, complex analysis may be required to identify the radio-frequency interference source, and to remove artifacts from the image on the basis of the characteristics of the radio-frequency interference source. When there are many radio-frequency interference sources or there are new types of radio-frequency interference, even more complexity is added to image processing, incurring more costs, and reducing the efficiency and/or effectiveness of image processing.

Figure 2:
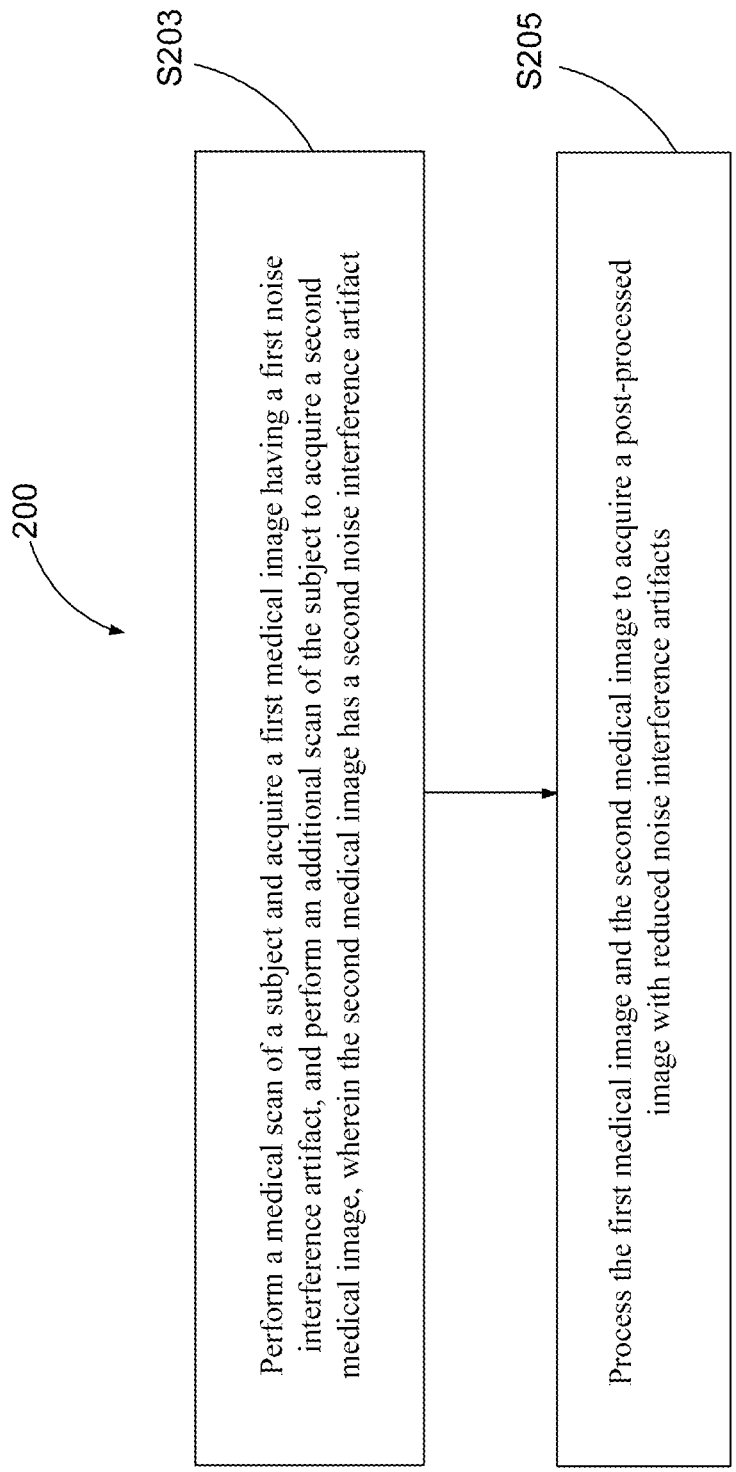
FIG. 2 illustrates a flowchart of a magnetic resonance imaging method according to some embodiments of the present invention.

FIG. 2 illustrates a flowchart 200 of a magnetic resonance imaging method according to some embodiments of the present invention, which may be implemented by applying the system shown in FIG. 1 or any variation thereof. In step S203, a medical scan is performed on the subject 16 and a first medical image having a first noise interference artifact is acquired, and an additional scan is performed on the subject 16 to acquire a second medical image, wherein the second medical image has a second noise interference artifact. In step S205, the first medical image and the second medical image are processed to acquire a post-processed image with reduced noise interference artifacts.

In one embodiment, the aforementioned processing is synthesis-related processing, which may include a variety of image processing techniques that use the first medical image and the second medical image to generate a post-processed image by means of a specific processing method. For example, data fusion of image data from the first medical image and the second medical image, deep learning of the first medical image and the second medical image, or data fusion and deep learning of the first medical image is performed to acquire a post-processed image that has the same region of interest as the first medical image and the second medical image and has reduced radio-frequency noise interference artifacts.

The medical scan may include a formal scan performed on the subject 16, the images of which are typically used for clinical diagnosis. Therefore, the removal of artifacts therein is generally key to the diagnostic evaluation of the patient. However, additional scans may be performed for images generated in any other stage or process of the scan (e.g., a positioning image), as long as it is necessary to remove artifacts therein that are associated with the embodiments of the present invention, so as to acquire a second medical image (where the noise interference artifacts are in a different location than the noise interference artifacts in the first medical image), and the aforementioned artifacts from the images are subsequently removed based on processing of the first medical image and the second medical image.

Figure 3:
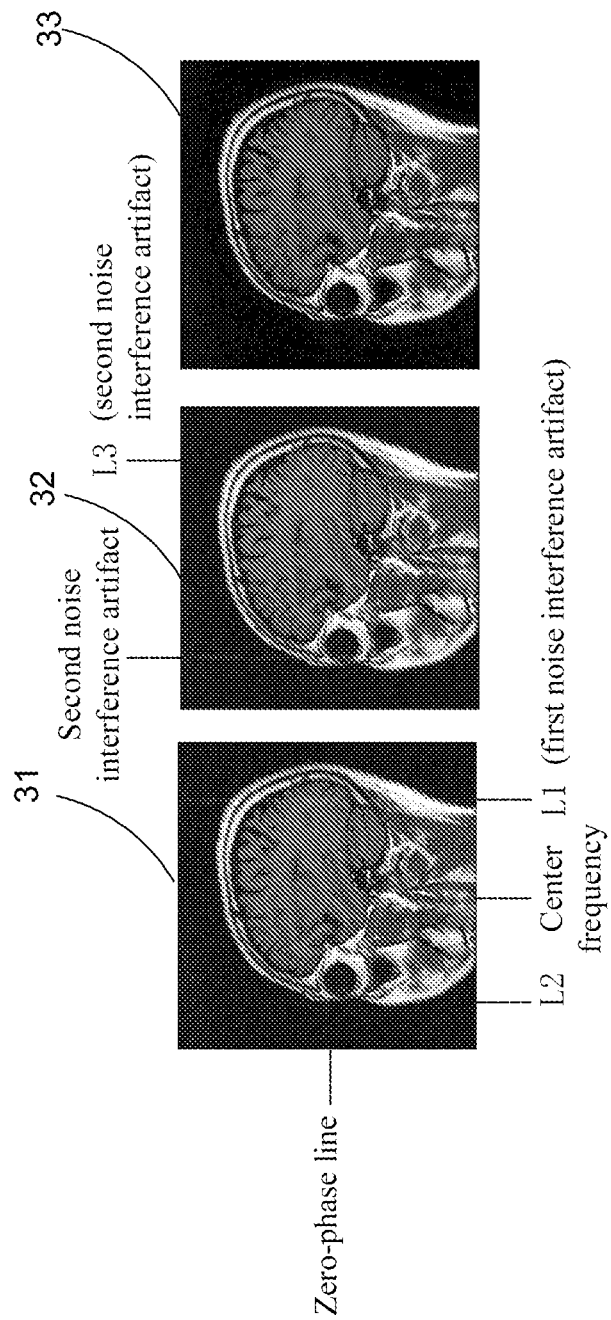
FIG. 3 illustrates a first medical image, a second medical image and a post-processed image, respectively.

FIG. 3 illustrates an example of a first medical image 31, which may be an image acquired during any of the scanning processes for performing an magnetic resonance examination, wherein chain-shaped noise interference artifacts appear. As the radio-frequency interference noise has a fixed frequency and is typically acquired in multiple (consecutive or intermittent) signal acquisition cycles, chain-shaped artifacts are formed in the image domain in the phase encoding direction (perpendicular to the frequency encoding direction). FIG. 3 further illustrates an example of a second medical image 32, which, as previously described, is acquired in an additional scan that may have the same scan part and substantially the same scan parameter settings as the medical scan described above, such that the data used to describe the tissue structure of the subject 16 in the second medical image 32 and the first medical image 31 are substantially the same.

The difference lies in that, noise interference artifacts appear in the second medical image 32 at a different location than they do in the first medical image 31, which may be achieved by changing a certain scan parameter, and this will be described in detail below. Specifically, the mapping location of the second noise interference artifact in the first medical image (e.g., location L2) is symmetrical to the location of the first noise interference artifact (L1) relative to a pixel center of the first medical image. The pixel center may be the location of an intersection of a zero-phase line and a center frequency line. As mentioned above, noise interference artifacts from the same source (or of the same frequency) are distributed in the phase encoding direction, so that the mapping location (L2) of the second noise interference artifact in the first medical image is symmetrical to the location L1 where the first noise is located, relative to the center frequency line. It may also be said that the mapping of the second noise interference artifact on the first medical image 31 is symmetrical or mirrored to the first noise interference artifact, relative to the center frequency line or the center of the image, e.g., the noise interference artifact of the first medical image and the noise interference artifact of the second medical image are located on two sides of the center frequency line and at equal distances from the center frequency line.

In one embodiment, the frequency encoding directions used in the aforementioned additional scan and medical scan are opposite, such that the first noise interference artifact and the second noise interference artifact are in a mirror-image or symmetrical relationship. Further, additional scans may be performed in any process before or after the medical scan, and other scanning processes may be performed between the additional scan and the medical scan.

Figure 4:
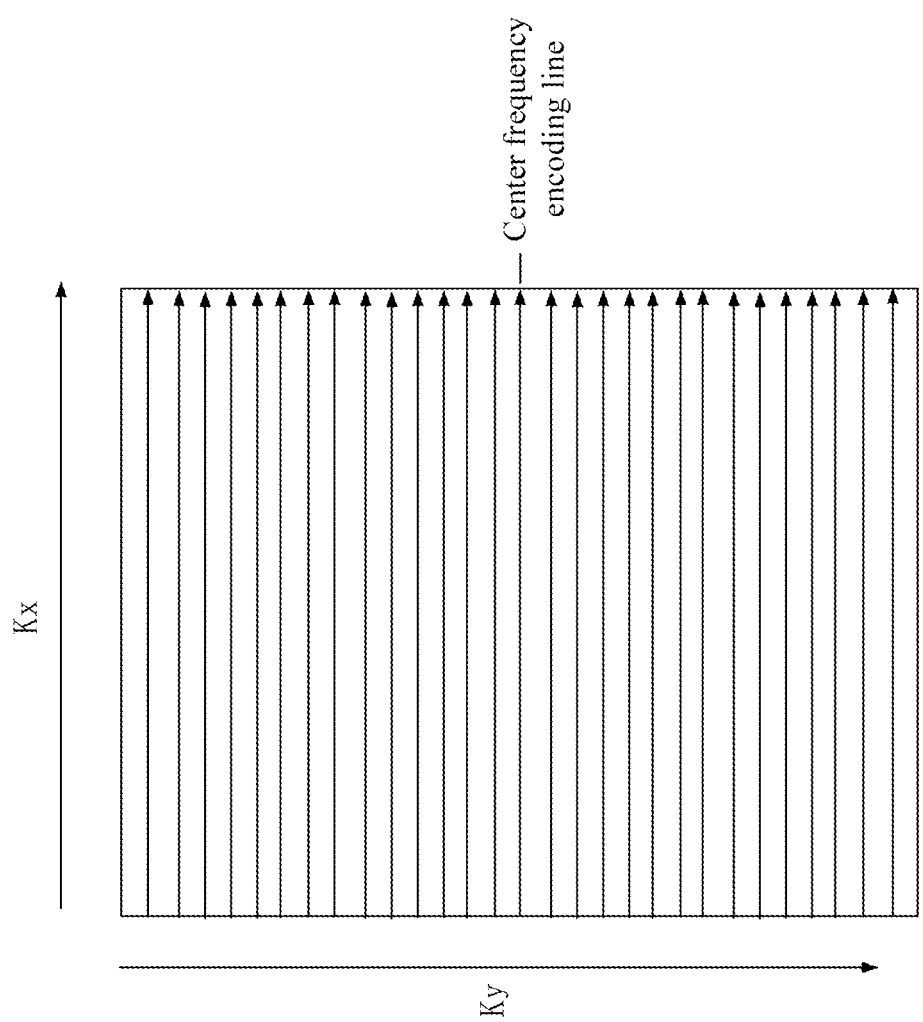
FIG. 4 illustrates an example of k-space encoding employed in a medical scan.
Figure 5:
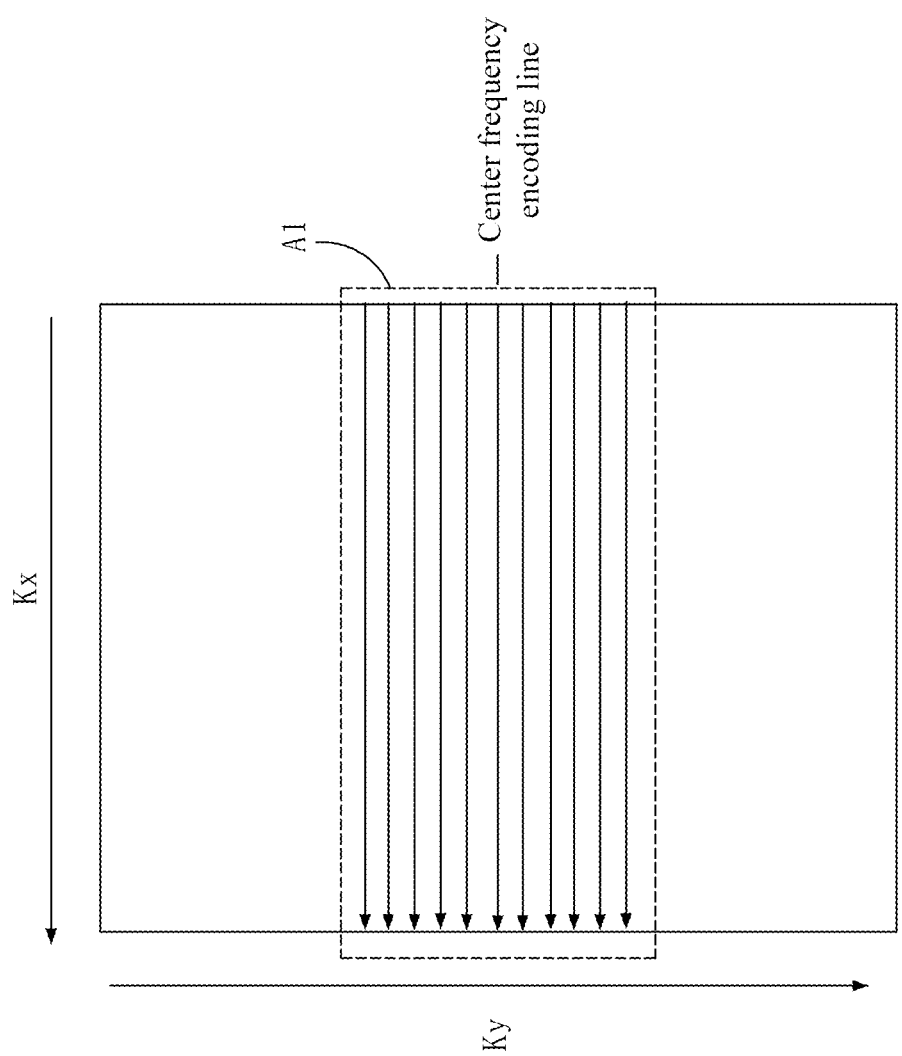
FIG. 5 illustrates an example of k-space encoding employed in an additional scan.

FIG. 4 illustrates an example of k-space encoding employed in a medical scan, and FIG. 5 illustrates an example of k-space encoding employed in an additional scan, wherein the frequency encoding direction in FIG. 5 is opposite to the frequency encoding direction Kx in FIG. 4, while the phase encoding directions Ky are the same. For example, in a medical scan, the gradient field applied in the frequency encoding direction gradually becomes larger, while in an additional scan, the gradient field applied in the frequency encoding direction gradually becomes smaller, or, in a medical scan, the gradient field applied in the frequency encoding direction gradually becomes smaller, while in an additional scan, the gradient field applied in the frequency encoding direction gradually becomes larger. This may be achieved by controlling the direction and/or magnitude of the drive current output from the gradient coil driver 115.

As mentioned above, one frequency encoding line is filled for each signal acquisition cycle (or within one repetition time of the scan sequence), and the more frequency encoding lines are acquired, the more image details may be presented in the reconstructed image. As additional scans take up additional examination time, in embodiments of the present invention, the time for additional scans may be shortened by down-sampling, i.e., acquiring less data compared with medical scans, e.g., filling only the frequency encoding lines in a central region A1 of the k-space. The center frequency line in the central region A1, for example, is centered on the central frequency encoding line. Data outside this center region are filled with 0. The second medical image 32 acquired in this manner has a lower resolution, but can be acquired in a shorter time.

FIG. 3 further illustrates an example of a post-processed image 33. As noise interference artifacts appear at different locations in the second medical image 32 compared with the first medical image, and the first noise interference artifacts are not present at the mapping location (L3) on the second medical image, one of the main objectives of processing the first medical image and the second medical image in step S205 is to use clean data free of the artifacts in each of the two images and perform data synthesis/fusion to acquire a post-processed image with reduced artifacts. For example, the first noise interference artifacts in the first medical image 31 are replaced with image data free of noise interference artifacts at the mapping location L3 on the second medical image 32, so as to reflect the anatomical structure of this location as realistically as possible while removing noise interference artifacts.

In one embodiment, in step S205, the first medical image 31 and the second medical image 32 are input into a trained first deep learning network for deep learning to acquire the post-processed image 33. The post-processed image 33 is output after inputting the first medical image 31 and the second medical image together into the deep learning network for deep learning.

The present embodiment achieves the main objective of the aforementioned processing by employing the first deep learning network. However, a person skilled in the art understands that other image processing techniques may also be used to achieve the aforementioned objectives. For example, in step S205, data fusion may be performed on the first medical image and the second medical image to acquire a post-processed image with reduced noise interference artifacts, wherein the data fusion may include specific pixel value-related operations, image stitching, etc.

Figure 6:
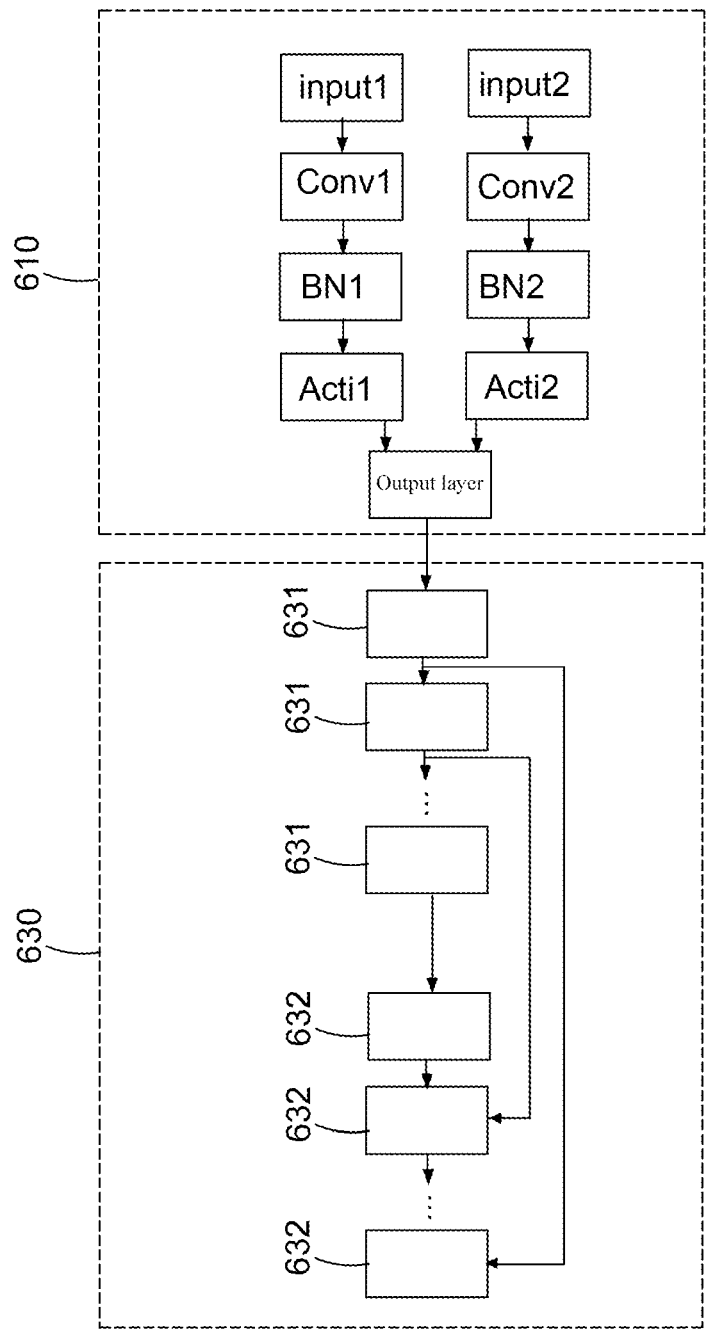
FIG. 6 illustrates a modular diagram of a first deep learning network according to an embodiment of the present invention.

FIG. 6 illustrates a modular diagram of a first deep learning network according to an embodiment of the present invention. The first deep learning network includes a pre-processing module 610 and a processing module 630, wherein the pre-processing module 610 is used to pre-process the first medical image 31 and the second medical image 32 respectively, and to perform data fusion of the pre-processed first medical image 31 and the pre-processed second medical image 31. The processing module 630 is used to process a result of the data fusion to output the post-processed image.

In one embodiment, the processing module 630 is used to perform a fusion operation on corresponding pixels of the pre-processed first medical image and the pre-processed second medical image, and the fusion operation may include, for example, adding pixel values.

In an exemplary embodiment, the pre-processing module 610 may have two branches, wherein the first branch includes, in turn, a first input terminal Input1 used to receive a first medical image, a first convolutional layer Conv1 used to perform convolutional processing of the first medical image, a first batch normalization layer BN1 used to perform batch normalization of the convolutionally processed image data, and a first activation layer Acti1 used to perform nonlinear mapping on output results from the batch normalization layer. The second branch includes, in turn, a second input terminal Input2 used to receive the second medical image, a second convolution layer Conv2 used to perform convolutional processing of the second medical image, a second batch normalization layer BN2 used to perform batch normalization of the convolutionally processed image data, and a second activation layer Acti2 used to perform nonlinear mapping on output results from the batch normalization layer. The pre-processing module 610 further includes an output layer used to output fused data of the output results of the first activation layer Acti1 and the second activation layer Acti2.

In an exemplary embodiment, the processing module 630 includes a generator network including a plurality of sequentially connected encoders 631 and a plurality of sequentially connected decoders 632. Each encoder 631 includes an input layer, a convolution layer, a batch normalization layer, an activation layer, and an output layer, wherein the input layer of the first encoder is used to receive the output result of the pre-processing module, i.e., the fused data, and each subsequent encoder is used to receive the output result of the previous encoder, so as to perform convolution, normalization, activation, etc. on such output results. Each decoder 632 includes two input terminals, a merge processing layer, a deconvolution layer, a batch normalization layer, an activation layer, and an output layer. Each decoder is in cascade connection with a symmetrical encoder, e.g., the first decoder cascades symmetrically with the last encoder, the second decoder cascades symmetrically with the penultimate encoder, the third decoder cascades symmetrically with the third to last encoder, and so on. One input terminal of each decoder is used to receive a feature map output by the previous decoder, and the other input terminal is used to receive a feature map to be merged (e.g., a feature map output by an encoder symmetrically cascaded with the decoder), and the merge processing layer is used to stitch the two feature maps together. The deconvolution layer is used to perform up-sampling of the stitching process results. The batch normalization layer is used to perform normalizing of the up-sampled results. The activation layer is used to perform nonlinear mapping on the normalized results, and the output layer is used to output a result of the nonlinear mapping.

The processing module 630 may further include a processing layer used to process the output result of the last decoder.

Embodiments of the present invention describe an exemplary structure of a first deep learning network, and in other embodiments, the first deep learning network may also have other structures. For example, the fusion of the first medical image and the second medical image may be skipped, and the post-processed image may be output directly by performing deep learning on the two medical images.

The aforementioned first deep learning network and a second deep learning network to be described below may be trained on the basis of a known input data set and a known output data set and by means of setting the number of neurons in the processing layers of the network, and optimizing network parameters (including but not limited to weights, biases, etc.) to identify the mathematical relationship between known inputs and desired outputs and to characterize the mathematical relationship between the inputs and outputs of each layer, so that the loss function converges, thereby acquiring the deep learning networks by training.

In one embodiment, the first deep learning network may be acquired by means of performing adversarial network-based training, wherein a plurality of image pairs (first images and second images) having mirrored noise interference artifacts can be used as first inputs and second inputs of a training data set, and images without noise interference artifacts (third images) can be used as outputs of the training data set to train the first deep learning network.

The adversarial network includes a generator, and the structure of the generator is similar to the network structure shown in FIG. 6. The adversarial network may further include a discriminator, which is used to receive an output image of the generator or a gold standard image, and to output a determination result as to whether the received image has noise interference artifacts.

The first image in the aforementioned image pair for the training data set may be an image having noise interference artifacts acquired in a clinical scan. The second image in the image pair may also be acquired by scanning. For example, if the first image is acquired based on a scan parameter setting, the second image may be acquired (before or after the acquisition of the first image) by means of the same parameter setting (changing only the frequency encoding direction), and the third image may be an artifact-free image acquired in a clinical scan as well, and may have the same anatomical site or region of interest as the first image and the second image.

Figure 7:
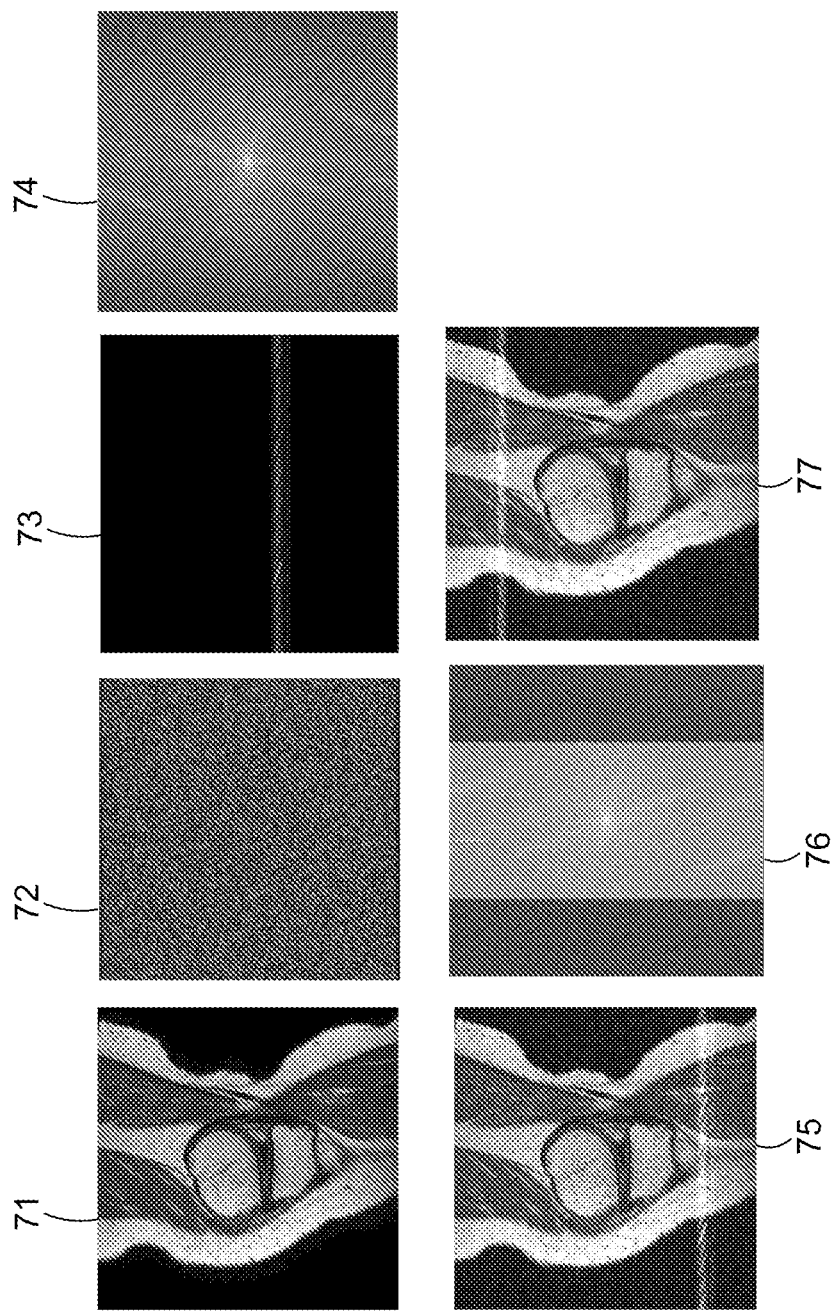
FIG. 7 illustrates a clinical image without interference noise or interference artifacts, a background noise image, a noise interference image, a first image, a third frequency domain image, a fourth frequency domain image and a second image, respectively.

Referring to FIG. 7, in other embodiments, the first input of the training data set, i.e., the first image, may also be acquired by synthesizing a noise interference image with a clinical image without noise interference artifacts. The following steps are specifically included:

In step 1, a clinical image without noise interference artifacts (e.g., image 71 in FIG. 7), a background noise image (e.g., image 72 in FIG. 7), and a noise interference image (e.g., image 73 in FIG. 7) are acquired.

In step 2, a noise interference image is synthesized based on an image with interference noise and the background noise image.

In step 3, the clinical image without noise interference artifacts is converted to a first frequency domain image.

In step 4, the synthesized noise interference image is converted to a second frequency domain image.

In step 5, a third frequency domain image (e.g., image 74 in FIG. 7) is synthesized based on the second frequency domain image and the first frequency domain image.

In step 6, the third frequency domain image is converted to a time domain image to serve as the first image described above (e.g., image 75 in FIG. 7).

With continued reference to FIG. 7, the second input of the training data set, i.e., the second image, may also be generated, and the following steps are specifically included:

In step 7, a mirrored noise interference image is acquired based on the synthesized noise interference image, wherein the interference noise in the mirrored noise interference image is at a location symmetrical (or mirrored) to the location of the noise interference in the original synthesized noise interference image.

In step 8, the mirrored noise interference image is converted to a fourth frequency domain image.

In step 9, the fourth frequency domain image is converted to a time domain image to serve as the second image described above.

Optionally, when a second image having a lower resolution is required for model training, after the acquisition of the fourth frequency domain image, the method may further include step 10, in which the fourth frequency domain image undergoes low-pass filtering so as to acquire a low-pass filtered fourth frequency domain image (e.g., image 76 shown in FIG. 7), and then in step 11, the low-pass filtered fourth frequency domain image is converted to a time domain image to serve as the second image having a lower resolution (e.g., image 77 shown in FIG. 7).

In one embodiment, although the configuration of the deep learning network is guided by dimensions such as prior knowledge, input, and output of an estimation problem, optimal approximation of required output data is implemented depending on or exclusively according to input data. In various alternative implementations, clear meaning may be assigned to some data representations in the deep learning network using some aspects and/or features of data, an imaging geometry, a reconstruction algorithm, or the like, which helps to speed up training. This creates an opportunity to separately train (or pre-train) or define some layers in the deep learning network.

In some embodiments, the first deep learning network described above and the second deep learning network to be described below are acquired based on training modules trained on an external carrier (e.g., a device other than the medical imaging system). In some embodiments, the training system may include a first module configured to store a training data set, a second module configured to perform training and/or update based on a model, and a communication network configured to connect the first module and the second module. In some embodiments, the first module includes a first processing unit and a first storage unit, where the first storage unit is configured to store the training data set, and the first processing unit is configured to receive a relevant instruction (for example, acquiring a training data set) and send the training data set according to the instruction. In addition, the second module includes a second processing unit and a second storage unit, where the second storage unit is configured to store a training model, and the second processing unit is configured to receive a relevant instruction and perform training and/or update of the network. In some other embodiments, the training data set may further be stored in the second storage unit of the second module, and the training system may not include the first module. In some embodiments, the communication network may include various connection types, such as wired or wireless communication links, or fiber-optic cables.

Once data (for example, a trained network) is generated and/or configured, the data can be replicated and/or loaded into the medical imaging system (for example, the magnetic resonance imaging system that will be described below), which may be accomplished in a different manner. For example, a model may be loaded via a directional connection or link between the medical imaging system and a computer. In this regard, communication between different elements may be accomplished using an available wired and/or wireless connection and/or based on any suitable communication (and/or network) standard or protocol. Alternatively or additionally, the data may be indirectly loaded into the medical imaging system. For example, the data may be stored in a suitable machine-readable medium (for example, a flash memory card), and then the medium is used to load the data into the medical imaging system (for example, by a user or an authorized person of the system on site); or the data may be downloaded to an electronic device (for example, a laptop computer) capable of local communication, and then the device is used on site (for example, by a user or an authorized person of the system) to upload the data to the medical imaging system via a direct connection (for example, a USB connector).

As discussed herein, the deep learning technology (also referred to as deep machine learning, hierarchical learning, deep structured learning, or the like) employs an artificial neural network for learning. The deep learning method is characterized by using one or a plurality of network architectures to extract or simulate data of interest. The deep learning method may be implemented using one or a plurality of processing layers (for example, an input layer, an output layer, a convolutional layer, a normalization layer, or a sampling layer, where processing layers of different numbers and functions may exist according to different deep network models), where the configuration and number of the layers allow a deep network to process complex information extraction and modeling tasks. Specific parameters (or referred to as "weight" or "bias") of the network are usually estimated through a so-called learning process (or training process). The learned or trained parameters usually result in (or output) a network corresponding to layers of different levels, so that extraction or simulation of different aspects of initial data or the output of a previous layer usually may represent the hierarchical structure or concatenation of layers. During image processing or reconstruction, this may be represented as different layers with respect to different feature levels in the data. Thus, processing may be performed layer by layer. That is, "simple" features may be extracted from input data for an earlier or higher-level layer, and then these simple features are combined into a layer exhibiting features of higher complexity. In practice, each layer (or more specifically, each "neuron" in each layer) may process input data as output data for representation using one or a plurality of linear and/or non-linear transformations (so-called activation functions). The number of the plurality of "neurons" may be constant among the plurality of layers or may vary from layer to layer.

Figure 8:
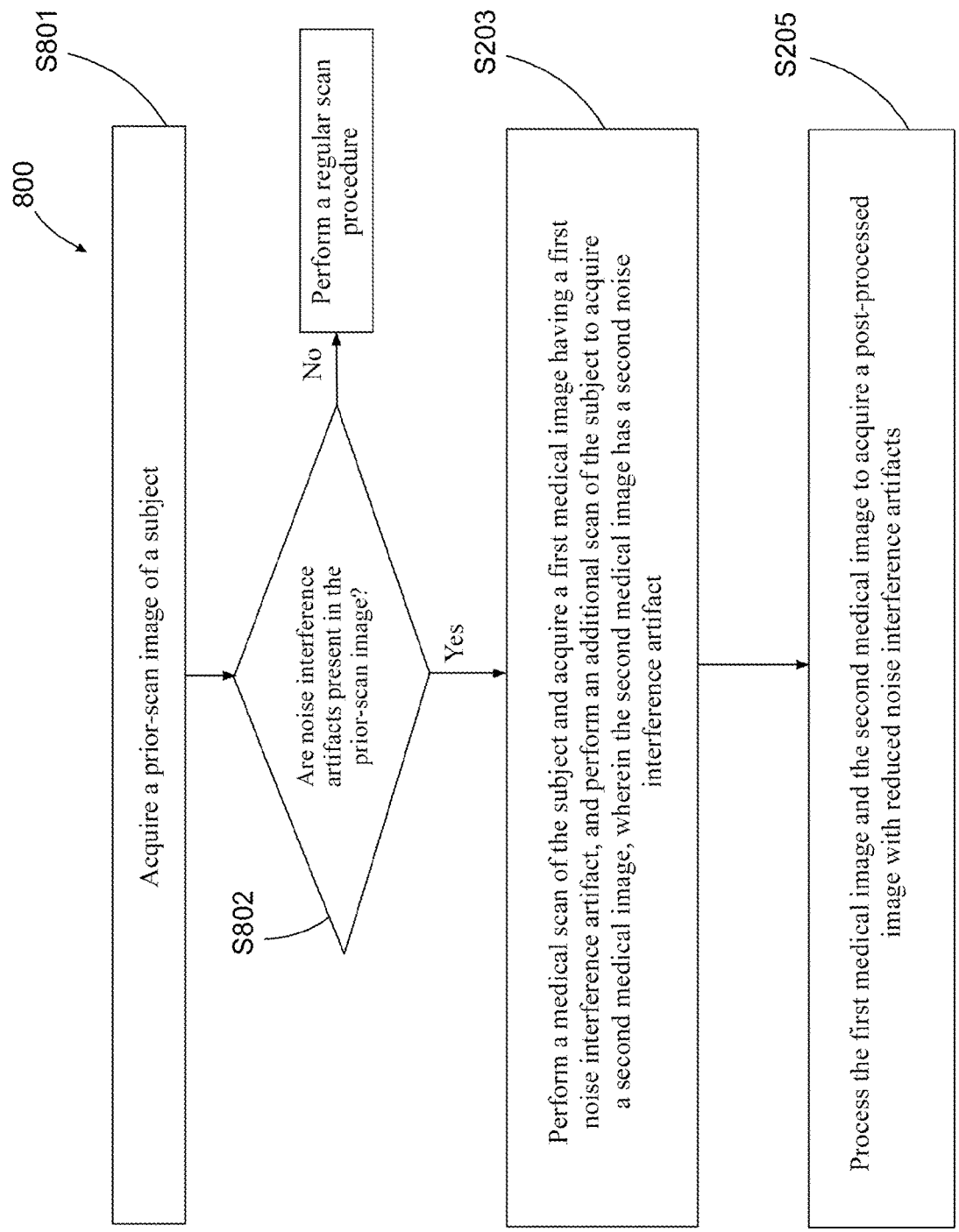
FIG. 8 illustrates a flowchart of a medical imaging method according to another embodiment of the present invention.

FIG. 8 illustrates a flowchart of a medical imaging method according to another embodiment of the present invention, which is similar to the method shown in FIG. 2, with the difference that step S801 and step S802 are included prior to step S203, i.e., prior to performing the first medical scan. In step S801, a prior-scan image of the subject is acquired. In step S802, it is determined whether there noise interference artifacts in the prior-scan image, and if so, step S205 is performed, i.e., a medical scan is performed on the subject to acquire the first medical image, and then the additional scan is performed on the subject to acquire the second medical image. If no artifacts are present in the prior-scan image, only a regular medical scan is performed and a medical image is acquired.

In this embodiment, firstly the presence of noise interference artifacts in the prior-scan is determined, then a process for removing noise interference artifacts is carried out, thereby avoiding redundant scanning processes and redundant image processing operations, so as to improve imaging efficiency.

In other embodiments, it is also possible to directly determine whether noise interference artifacts are present in the first medical image, and if so, the additional scan is initiated and subsequent artifact removal processing is carried out. However, in a magnetic resonance scan process, processes such as pre-scanning, positioning scanning, etc. are generally performed to acquire prior-scan images before clinical diagnostic images are acquired. The determination of the prior-scan image may make it possible to prepare for additional scans and image post-processing in advance, and the determination of the prior-scan image may be performed simultaneously during the execution of other scanning tasks, thereby saving magnetic resonance examination time and avoiding the time spent waiting for determinations to be made between the medical scans and additional scans.

As previously shown, the medical scan may include a formal scan. The prior-scan image may include a pre-scan image acquired by pre-scanning the subject, such as a shimming image for uniformity analysis and conditioning of the primary magnetic field. The prior-scan image may also include a positioning image. In other embodiments, the image acquired from the formal scan may also be used as a prior-scan image for other subsequent medical scans.

In one embodiment, it may be determined whether there are noise interference artifacts in the prior-scan image on the basis of a trained second deep learning network, and an existing deep learning network may be selected for data set training to acquire the second deep learning network, which will not be repeated herein.

Embodiments of the present invention may also provide a computer-readable storage medium including a stored computer program, wherein the magnetic resonance imaging method in any of the aforementioned embodiments is executed when the computer program is run.

Figure 9:
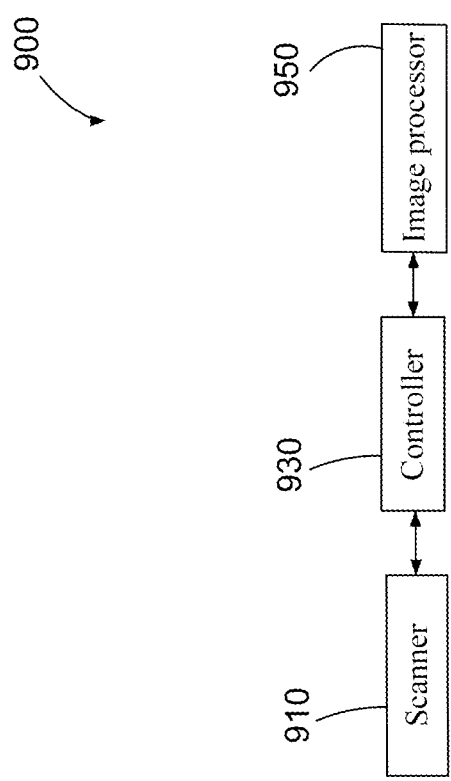
FIG. 9 illustrates a block diagram of a magnetic resonance imaging system according to an embodiment of the present invention.

FIG. 9 illustrates a block diagram 900 of a magnetic resonance imaging system according to an embodiment of the present invention, which may include some or all of the components of the system 100 shown in FIG. 1. For example, the system 900 includes a scanner 910, a controller 930, and an image processor 950. The controller 930 is used to control the scanner 910 to perform a magnetic resonance scan, which comprises: performing a medical scan of a subject and acquiring a first medical image, the first medical image having a first noise interference artifact; and performing an additional scan of the subject to acquire a second medical image, wherein the second medical image has a second noise interference artifact. The mapping location of the second noise interference artifact in the first medical image is symmetrical to the location of the first noise interference artifact relative to a pixel center of the first medical image. The image processor is used to process the first medical image and the second medical image to acquire a post-processed image with reduced noise interference artifacts.

In one embodiment, the controller 930 is used to control the scanner to use opposite frequency encoding directions when performing the additional scan and the medical scan so that the second noise interference artifact is symmetrical or mirrored to the first noise interference artifact relative to the pixel center of the image.

In one embodiment, the resolution of the second medical image is lower than the resolution of the first medical image. Since it takes less time to acquire a lower resolution image, the time required to perform additional scans may be reduced. For example, the controller 930 may control the scanner 910 to capture less data when performing additional scans as compared with medical scans. Specifically, data near a center frequency encoding line in the k-space (e.g., low frequency data in the central region of the k-space) can be sampled, while data outside of the central region/data at more marginal frequency encoding lines (e.g., high frequency data near the edges) are not sampled, and are filled with 0.

In one embodiment, the image processor 950 includes a trained first deep learning network used to perform deep learning on the first medical image and the second medical image to output the post-processed image.

In one embodiment, the first deep learning network includes a pre-processing module and a processing module. The pre-processing module is used to pre-process the first medical image and the second medical image respectively, and to perform data fusion of the pre-processed first medical image and the pre-processed second medical image. The processing module is used to process a result of the data fusion to output the post-processed image.

In one embodiment, the data fusion comprises: performing a fusion operation on corresponding pixel values of the pre-processed first medical image and the pre-processed second medical image.

In one embodiment, the first deep learning network is acquired by means of performing adversarial network-based training.

Figure 10:
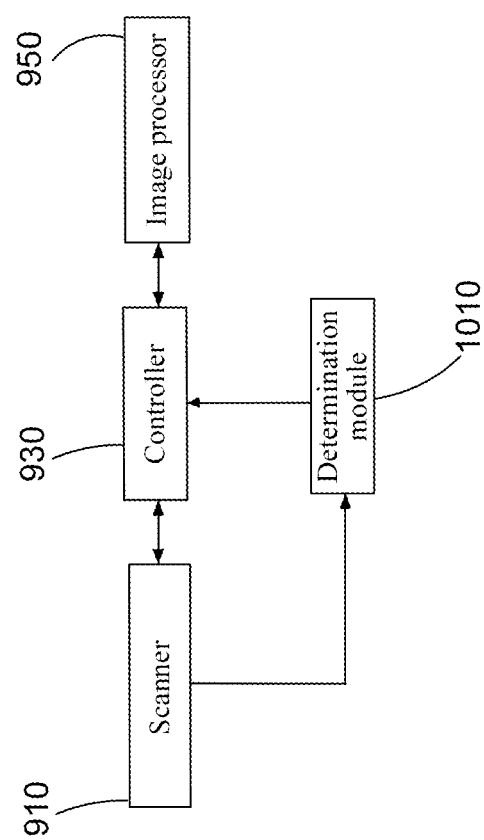
FIG. 10 illustrates a block diagram of a magnetic resonance imaging system according to another embodiment of the present invention.

FIG. 10 illustrates a block diagram of a magnetic resonance imaging system according to another embodiment of the present invention, which is similar to the system shown in FIG. 9, with the difference that a determination module 1010 is further included. In this embodiment, the controller 930 is further used to control the scanner to acquire a prior-scan image of the subject prior to performing the medical scan. The determination module 1010 is used to determine whether there are noise interference artifacts in the prior-scan image, and if so, the controller 930 controls the scanner to perform a medical scan of the subject and acquire a first medical image, and then perform an additional scan of the subject to acquire a second medical image. The determination module 1010 may be a module independent of the controller 930 or integrated with the controller 930 as part of the controller 930.

In one example, the controller 930 may first control the scanner to perform a prior-scan, then control the scanner to perform a medical scan, and perform an additional scan when it is considered (for example, by means of performing a determination of the prior-scan image) that the medical image acquired by the medical scan will have noise interference artifacts. The prior-scan image may include a pre-scan image acquired by pre-scanning the subject, or a positioning image as described above, and the pre-scan image may include a shimming image or an image for other applications.

In one embodiment, the determination module 1010 includes a trained second deep learning network used to perform deep learning on the prior-scan image to determine whether a noise interfering image is present therein.

In each embodiment of the present invention, in order to reduce the noise interference artifacts of the first medical image acquired in a medical scan, an additional scan is performed on the subject to acquire a second medical image, and the noise interference artifacts in the second medical image are arranged to have a different location (e.g., coordinates in the image) than the noise interference artifacts in the first medical image, and a post-processed image with reduced artifacts is acquired based on the first and second images, thereby avoiding missing or inaccurate/incomplete restoration of anatomical image data brought about by removing artifacts of the first medical image alone, and making it possible to reflect the anatomical structure at the artifact location as realistically as possible while removing the noise interference artifacts.

Figure 11:
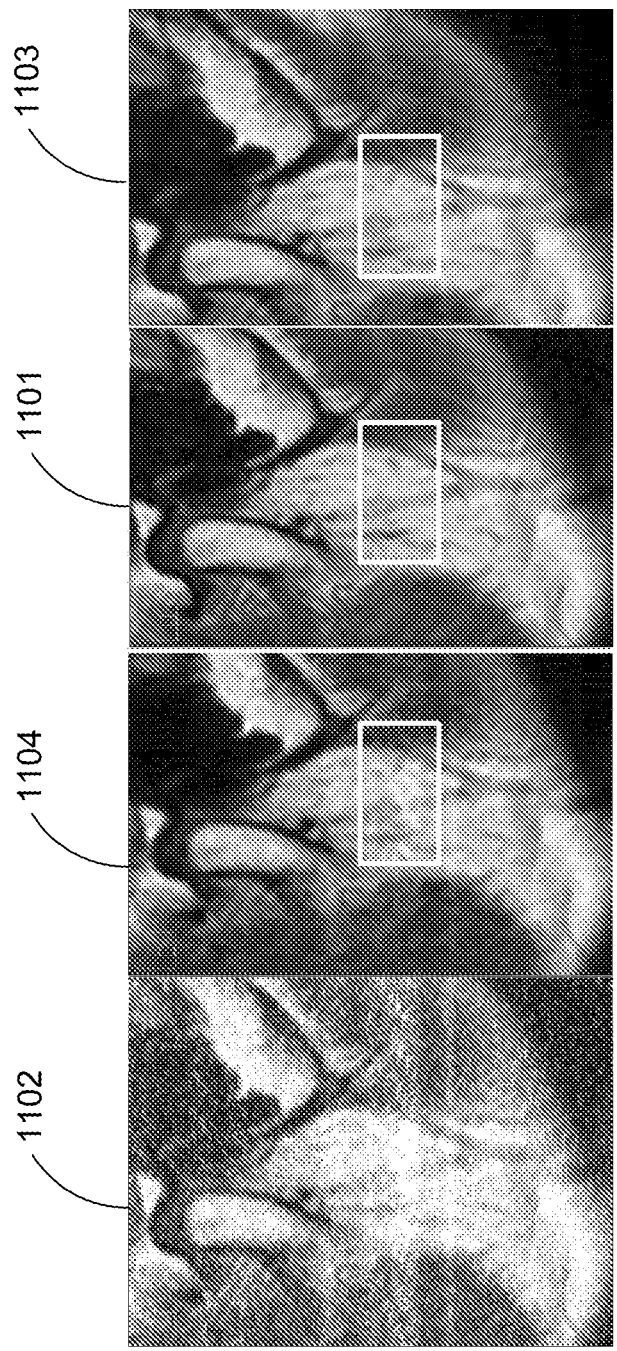
FIG. 11 illustrates a gold standard image of a body part of the human body, an original image having noise interference artifacts, a post-processed image acquired based on an embodiment of the present invention, and a post-processed image acquired solely based on a first medical image, respectively.

In each embodiment of the present invention, images with better artifact removal effects can be acquired without analyzing the noise source that produces the noise interference artifacts. In order to verify the technical effectiveness of the present invention, comparative imaging experiments were conducted for at least six parts of the human body. As shown in FIG. 11, a gold standard image 1101 of a part, an original image 1102 having noise interference artifacts, and a post-processed image 1103 acquired based on the embodiments of the present invention are illustrated. Observing the white framed areas in the images of FIG. 11, it can be seen that noise interference artifacts have been largely removed from the post-processed image 1103 when compared with the original image 1102, and the post-processed image 1103 more closely resembles the gold standard image 1101. In the above embodiments of the present invention, a post-processed image is acquired based on the first medical image and the second medical image. In addition, FIG. 11 further illustrates a post-processed image 1104 acquired solely based on the first medical image (for example, similar image processing is carried out on said image), and it is clear through a comparison of the images 1101, 1102, 1103, and 1104 that although noise interference artifacts are reduced in the image 1104 when compared with the original image 1102, the post-processed image 1104 has a better artifact removal effect and more closely resembles the gold standard image.

In addition, through experiments and analyses, it has been found that the post-processed image acquired based on the embodiments of the present invention has significant advantages over a post-processed image acquired solely based on a single image in terms of other metrics as well, such as the mean square error (MSE), peak signal-to-noise ratio (PSNR) and structural similarity (SSIM) of the image.

The purpose of providing the above specific embodiments is to facilitate understanding of the content disclosed in the present invention more thoroughly and comprehensively, but the present invention is not limited to these specific embodiments. Those skilled in the art should understand that various modifications, equivalent replacements, and changes can also be made to the present invention and should be included in the scope of protection of the present invention as long as these changes do not depart from the spirit of the present invention.

The invention claimed is:

1. A magnetic resonance imaging method, comprising:
performing a medical scan of a subject and acquiring a first medical image having a first noise interference artifact, and performing an additional scan of the subject to acquire a second medical image, wherein the second medical image has a second noise interference artifact, and the location mapping of the second noise interference artifact in the first medical image is symmetrical to the location of the first noise interference artifact relative to a pixel center of the first medical image; and performing synthesis-related processing on the first medical image and the second medical image to acquire a post-processed image with reduced noise interference artifacts.

2. The method according to claim 1, wherein frequency encoding directions used in the additional scan and in the medical scan are opposite.

3. The method according to claim 2, wherein the second medical image has a lower resolution than the first medical image.

4. The method according to claim 3, wherein a central region passing through a center frequency line in k-space is sampled when the additional scan is performed, and data outside the central region are filled with 0.

5. The method according to claim 1, wherein the step of performing synthesis-related processing on the first medical image and the second medical image comprises:
inputting the first medical image and the second medical image into a trained first deep learning network for deep learning to acquire the post-processed image.

6. The method according to claim 5, wherein the first deep learning network comprises:
a pre-processing module used to pre-process the first medical image and the second medical image respectively and to perform data fusion of the pre-processed first medical image and the pre-processed second medical image; and,
a processing module used to process a result of the data fusion to output the post-processed image.

7. The method according to claim 6, wherein the data fusion comprises: performing a fusion operation on corresponding pixel values of the pre-processed first medical image and the pre-processed second medical image.

8. The method according to claim 5, wherein the step of performing synthesis-related processing on the first medical image and the second medical image comprises:
performing fusion processing on the first medical image and the second medical image to acquire the post-processed image.

9. The method according to claim 1, further comprising:
acquiring a prior-scan image of the subject prior to performing the medical scan;
determining whether noise interference artifacts are present in the prior-scan image, and if so, performing the additional scan of the subject to acquire the second medical image.

10. The method according to claim 9, wherein the prior-scan image comprises a pre-scan image acquired by pre-scanning the subject.

11. The method according to claim 10, wherein the pre-scan image comprises a shimming image.

12. The method according to claim 9, wherein the prior-scan image comprises a positioning image.

13. The method according to claim 9, wherein the presence or absence of noise interference artifacts in the prior-scan image is determined based on a trained second deep learning network.

14. A non-transitory computer-readable storage medium, comprising a stored computer program, wherein the method of claim 1 is executed when the computer program is run.

15. A magnetic resonance imaging system, comprising:
a scanner;
a processing system programmed to control the scanner to perform a magnetic resonance scan, the magnetic resonance scan comprising:
performing a medical scan of a subject and acquiring a first medical image, wherein the first medical image has a first noise interference artifact; and
performing an additional scan of the subject to acquire a second medical image, wherein the second medical image has a second noise interference artifact, and the location mapping of the second noise interference artifact in the first medical image is symmetrical to the location of the first noise interference artifact relative to a pixel center of the first medical image; and,
an image processor used to perform synthesis-related processing on the first medical image and the second medical image to acquire a post-processed image with reduced noise interference artifacts.

16. The system according to claim 15, wherein the processing system is programmed to control the scanner to use opposite frequency encoding directions when performing the additional scan and the medical scan.

17. The system according to claim 16, wherein the second medical image has a lower resolution than the first medical image.

18. The system according to claim 15, wherein the image processor comprises a trained first deep learning network used to perform deep learning on the first medical image and the second medical image to output the post-processed image.

19. The system according to claim 18, wherein the first deep learning network comprises a pre-processing module and a processing module, wherein the pre-processing module is used to pre-process the first medical image and the second medical image respectively and to perform data fusion of the pre-processed first medical image and the pre-processed second medical image, and the processing module is used to process a result of the data fusion to output the post-processed image.

20. The system according to claim 15, wherein the processing system is further programmed to control the scanner to acquire a prior-scan image of the subject prior to performing the medical scan, and the magnetic resonance imaging system further comprises a determination module used to determine whether noise interference artifacts are present in the prior-scan image, and if so, the controller controls the scanner to perform the additional scan of the subject to acquire the second medical image.

* * * * *